United States Patent
Mrsny et al.

(10) Patent No.: US 9,090,691 B2
(45) Date of Patent: Jul. 28, 2015

(54) SYSTEMS AND METHODS OF DELIVERY OF BIOACTIVE AGENTS USING BACTERIAL TOXIN-DERIVED TRANSPORT SEQUENCES

(75) Inventors: Randall J. Mrsny, Los Altos Hills, CA (US); Tahir Mahmood, San Francisco, CA (US)

(73) Assignee: APPLIED MOLECULAR TRANSPORT LLC, Burlingame, CA (US)

(*) Notice: Subject to any disclaimer, the term of this patent is extended or adjusted under 35 U.S.C. 154(b) by 0 days.

(21) Appl. No.: 13/822,435

(22) PCT Filed: Sep. 15, 2011

(86) PCT No.: PCT/US2011/001602
§ 371 (c)(1),
(2), (4) Date: Mar. 12, 2013

(87) PCT Pub. No.: WO2012/036746
PCT Pub. Date: Mar. 22, 2012

(65) Prior Publication Data
US 2013/0172229 A1 Jul. 4, 2013

Related U.S. Application Data

(60) Provisional application No. 61/403,394, filed on Sep. 15, 2010.

(51) Int. Cl.
*A61K 47/48* (2006.01)
*C07K 14/28* (2006.01)
(Continued)

(52) U.S. Cl.
CPC .............. *C07K 14/28* (2013.01); *A61K 9/5184* (2013.01); *A61K 31/711* (2013.01);
(Continued)

(58) Field of Classification Search
CPC ............... C07K 14/28; C07K 16/1239; C07K 2319/10; C07K 2319/33; A61K 47/48246; A61K 47/48261; A61K 47/48484; A61K 47/48561; A61K 47/48569
See application file for complete search history.

(56) References Cited

U.S. PATENT DOCUMENTS 2,643,653 A * 6/1953 Heidrich .......................... 604/62
7,713,737 B2 5/2010 Mrsny
(Continued)

FOREIGN PATENT DOCUMENTS

WO WO 2009014650 A2 * 1/2009
WO 2009026328 A2 2/2009
(Continued)

OTHER PUBLICATIONS

Shiraishi et al, Enhanced delivery of cell-penetrating peptide-peptide nucleic acid conjugates by endosomal disruption, Nature Protocols (2006) vol. 1(2) 1-4.*
(Continued)

*Primary Examiner* — Christina Bradley
*Assistant Examiner* — Randall L Beane
(74) *Attorney, Agent, or Firm* — Craig A Crandall (57) ABSTRACT

The field of the present invention relates, in part, to a strategy for novel pharmaceutical applications. More specifically, the present invention relates to a genetically detoxified form of *Vibrio cholera* exotoxin (cholix) and the use of cholix-derived polypeptide sequences to enhance intestinal delivery of biologically-active therapeutics. Importantly, the systems and methods described herein provide for the following: the ability to deliver macromolecule doses without injections; the ability to deliver cargo, such as (but not limited to) siRNA or antisense molecules into intracellular compartments where their activity is required; and the delivery of nanoparticles and dendrimer-based carriers across biological membranes, which otherwise would have been impeded due to the barrier properties of most such membranes.

12 Claims, 2 Drawing Sheets

(51) Int. Cl.

| | | |
|---|---|---|
| *A61K 9/51* | (2006.01) | |
| *C07K 14/435* | (2006.01) | |
| *A61K 38/21* | (2006.01) | |
| *A61K 38/27* | (2006.01) | |
| *A61K 38/28* | (2006.01) | |
| *A61K 31/7105* | (2006.01) | |
| *A61K 31/713* | (2006.01) | |
| *A61K 31/711* | (2006.01) | |
| *C07K 19/00* | (2006.01) | |

(52) U.S. Cl.
CPC .......... *A61K 31/713* (2013.01); *A61K 31/7105* (2013.01); *A61K 38/212* (2013.01); *A61K 38/27* (2013.01); *A61K 38/28* (2013.01); *A61K 47/48246* (2013.01); *A61K 47/48261* (2013.01); *C07K 14/43595* (2013.01); *C07K 19/00* (2013.01); *C07K 2319/10* (2013.01); *C07K 2319/33* (2013.01); *C07K 2319/50* (2013.01)

(56) References Cited

U.S. PATENT DOCUMENTS

| | | |
|---|---|---|
| 2009/0148401 A1 | 6/2009 | Mrsny |
| 2010/0151005 A1 | 6/2010 | Muro-Galindo et al. |
| 2010/0196277 A1 | 8/2010 | DeSimone et al. |
| 2011/0250199 A1 | 10/2011 | Fitzgerald et al. |

FOREIGN PATENT DOCUMENTS

| | | |
|---|---|---|
| WO | 2009115531 A2 | 9/2009 |
| WO | 2009149281 A1 | 10/2009 |

OTHER PUBLICATIONS

Jeong et al., Bioconjugate Chem., vol. 20:5-14 (Nov. 17, 2008).*
Jorgensen et al., J. Biol. Chem., vol. 283:10671-10678 (Feb. 14, 2008).*
Baseman and Collier, Infection and Immunity, 10(5):1146-1151, 1974.
Deng and Barbieri, Annu Rev Microbiol, 62:271-288, 2008.
Fitzgerald et al., Journ of Cell Biology, 129(6):1533-1541, 1995.
Jorgensen et al., Journ of Biol. Chem., 283(16):10671-10678, 2008.
Mrsny et al., Drug Discovery Today, 7(4):247-258, 2002.
PCT International Search Report and Written Opinion, PCT/US2011/001602, dated Feb. 6, 2012.
Yates et al., Trends Biochem Sci, 31:123-133, 2006.
Jeong et al., Bioconjugate Chem., 20:5-14, 2009 (published online Nov. 2008).
Sarnovsky et al., Cancer Immunol. Immunother., 59:737-746, 2010 (published online Nov. 2009).
Weldon and Pastan, FEBS J., 278(23):4683-4700, Dec. 2011.

* cited by examiner

FIG. 1

FIG. 2

SYSTEMS AND METHODS OF DELIVERY OF BIOACTIVE AGENTS USING BACTERIAL TOXIN-DERIVED TRANSPORT SEQUENCES

RELATED PATENT APPLICATIONS

This application is the 371(c) national phase entry of PCT application PCT/US2011/001602 having an international filing date of Sep. 15, 2011, which claims benefit of U.S. Provisional Application No. 61/403,394, filed on Sep. 15, 2010, each incorporated in its entirety by reference herein.

TECHNICAL FIELD

The field of the present invention relates, in part, to a strategy for novel pharmaceutical applications. More specifically, the present invention relates to a non-toxic mutant form of the *Vibrio cholera* Cholix gene (ntCholix), a variant of Cholix truncated at amino acid $A^{386}$ (Cholix$^{386}$) and the use of other various Cholix-derived polypeptide sequences to enhance intestinal delivery of biologically-active therapeutics. Importantly, the systems and methods described herein provide for the following: the ability to deliver macromolecule doses without injections; the ability to deliver cargo, such as (but not limited to) siRNA or antisense molecules into intracellular compartments where their activity is required; and the delivery of nanoparticles and dendrimer-based carriers across biological membranes, which otherwise would have been impeded due to the barrier properties of most such membranes.

BACKGROUND ART

The majority of currently-approved small molecule drugs are absorbed across the mucosa of the small intestine to provide delivery to the systemic circulation. In fact, small molecule drugs are selected based upon their stability and efficient absorption across intestinal mucosae. A similar oral delivery of biologically-active polypeptides (referring to a polymer composed of amino acid residues; typically defined as a protein or peptide) has been a long-standing goal of the pharmaceutical industry. As the gastrointestinal (GI) tract is designed to digest dietary proteins and peptides, there are numerous physical, physiological, and biological barriers that limit the feasibility of therapeutic proteins and peptides uptake from the intestine in a manner similar to that achievable with small molecules; Mahato, R. I., et al., *Crit Rev Ther Drug Carrier Syst*, 20(2-3):p. 153-214 (2003).

A number of technologies have been identified that can be used to protect therapeutic proteins and peptides through the stomach, allowing them to reach the absorptive surface of epithelial cells in the small intestine and separating them from the gastric and intestinal environments that function to destroy dietary proteins and peptides. Unfortunately, however, the efficient transport across this simple, single layer of cells remains a substantial barrier due to the intracellular trafficking to destructive lysosome compartments after endosomal uptake of polypeptides at the luminal surface; Woodley, J. F., *Crit Rev Ther Drug Carrier Syst*, 11(2-3):p. 61-95 (1994). Indeed, this barrier is designed to inhibit uptake of proteins and peptides until these macromolecules can be sufficiently degraded for absorption through amino acid and di- or tri-peptide transporters. In this regard, a number of efforts have been examined to overcome the physical, physiological, and biological barriers of the intestinal mucosae.

There are two basic routes across the simple epithelium that constitutes the cellular barrier of the intestinal mucosae. Specifically, once across the covering mucus layer, a molecule could move between adjacent epithelial cells (paracellular route) or move through cells (transcellular route) via a series of vesicles that traffic within, but do not mingle, contents with the cytoplasm; T. Jung et al., *Eur J Pharm Biopharm*, 50:147-160 (2000). In other words, in both routes, a transport protein or peptide therapeutic does not enter into the cell but rather stays in an environment external to the cell's cytoplasm.

The primary barrier to casual movement of therapeutic protein and peptide movement through the paracellular route is a complex of proteins at the apical neck of these cells known as the tight junction (TJ). While transient opening and closing of TJ structures can facilitate transport of peptides across intestinal epithelia, this approach has key limitations: e.g., it does not work well for molecules above ~5 kDa; it has the potential for non-selective entry of materials into the body from the intestinal lumen; and it represents a route that involves only a small fraction of the surface area of the intestinal epithelium.

The primary barrier to casual migration of protein or peptide therapeutics across cells via the transcellular route is a default vesicle trafficking that delivers the contents of these vesicles to a destructive (lysosomal) pathway. As compared to the paracellular route, movement through the vesicular transcellular route can accommodate materials as large as 100 nm in diameter, involves essentially the entire epithelial cell surface, and can be highly selective in uptake of materials through the use of receptor-ligand interactions for vesicle entry. Thus, the transcellular route is very appealing for the epithelial transport of protein or peptide therapeutics if the destructive pathway can be avoided.

Some pathogens have solved the trafficking barrier problem, as demonstrated by the efficient transcytosis of secreted polypeptide virulence factors which function to facilitate and/or stabilize infection of a host. Exotoxins represent a class of proteins released by a variety of microorganisms which function as potent virulence factors. Exotoxins function on multicellular organisms with the capacity to acts as potent toxins in man; Roszak, D. B., and Colwell, R. R., *Microbiol Rev* 51:365-379 (1987). These proteins commonly kill or inactivate host cells through mechanisms that involve selective disruption of protein synthesis. Accordingly, only a few molecules are required to kill, consistent with the observation that bacterial exotoxins are some of the most toxic agents known. A subset of these proteins comprised of the family of proteins that consists of diphtheria toxin (DT) from *Corynebacterium diphtheria*, exotoxin A from *Pseudomonas aeruginosa* (PE), and a recently identified protein termed Cholix from *Vibrio cholera* function to intoxicate host cells via the ADP-ribosylation of elongation factor 2 (EF2); Yates, S. P., et al., *Trends Biochem Sci*, 31:123-133 (2006). These exotoxins are synthesized as a single chain of amino acids that fold into distinct domains that have been identified as having specific functions in targeting, entry, and intoxication of host cells.

The biology of exotoxin A from *Pseudomonas aeruginosa* (PE) has recently been described; Mrsny, R. J., et al., *Drug Discov Today*, 7(4): p. 247-58 (2002). PE is composed of a single chain of 613 amino acids having a theoretical molecular weight (MW) of 66828.11 Da, an isoelectric point (pI) of 5.28, and that functionally folds into three discrete domains, denoted domain I ($Ala^1$-$Glu^{252}$), domain II ($Gly^{253}$-$Asn^{364}$), domain III ($Gly^{405}$-$Lys^{613}$), and which contains a ADP-ribosyltransferase activity site), and a short disulfide-linked loop linking domains II and III which is known as the Ib loop ($Ala^{365}$-$Gly^{404}$). The organization of these domains at pH 8.0 have determined from crystal diffraction at a resolution of ~1.5 Å; Wedekind, J. E. et al., *J Mol Biol*, 314:823-837 (2001). Domain I (Ia+Ib) has a core formed from a 13-stranded β-roll, domain II is composed of six α-helices, and domain III has a complex α/β-folded structure. Studies have supported the idea that the modular nature of PE allows for distinct domain functions: domain I binds to host cell receptors, domain II is involved in membrane translocation, and domain III functions as an ADP-ribosyltransferase. It appears that PE is secreted by *P. aeruginosa* in close proximity to the epithelial cell apical surface, possibly in response to environmental cues and/or cellular signals; Deng, Q. and J. T. Barbieri, *Annu Rev Microbiol*, 62:p. 271-88 (2008). Once secreted, internalization into cells occurs after domain I of PE binds to the membrane protein α2-macroglobulin, a protein which is also known as the low-density lipoprotein receptor-related protein 1 (LRP1) or CD91; see, e.g., FitzGerald, D. J., et al., *J Cell Biol*, 129(6):p. 1533-41 (1995); Kounnas, M. Z., et al., *J Biol Chem*, 267(18): p. 12420-3 (1992). Following internalization, PE avoids trafficking to the lysosome and is instead efficiently delivered to the basolateral surface of the cell where it is released in a biologically-active form; Mrsny, R. J., et al., *Drug Discov Today*, 7(4): p. 247-58 (2002). Once across the epithelium, PE functions as a virulence factor by entering into CD91-positive cells within the submucosal space (macrophage and dendritic cells) where it then intersects with an unfolding pathway that leads to the cytoplasmic delivery of domain III; see, e.g., Mattoo, S., Y. M. Lee, and J. E. Dixon, *Curr Opin Immunol*, 19(4): p. 392-401 (2007); Spooner, R. A., et al., *Virol J*, 3: p. 26 (2006).

*Vibrio cholerae* bacterium is best known for its eponymous virulence agent, cholera toxin (CT), which can cause acute, life-threatening massive watery diarrhea. CT is a protein complex composed of a single A subunit organized with a pentamer of B subunits that binds to cell surface $G_{M1}$ ganglioside structures at the apical surface of epithelia. CT is secreted by *V. cholera* following horizontal gene transfer with virulent strains of *V. cholerae* carrying a variant of lysogenic bacteriophage called CTXf or $CTX_\phi$. Recent cholera outbreaks, however, have suggested that strains of some serogroups (non-O1, non-O139) do not express CT but rather use other virulence factors. Detailed analyses of non-O1, non-O139 environmental and clinical data suggested the presence of a novel putative secreted exotoxin with some similarity to PE.

Jorgensen, R. et al., *J Biol Chem*, 283(16):10671-10678 (2008) reported that some strains of *V. cholerae* did, in fact, contain a protein toxin having similarity to PE and which they termed Cholix toxin (Cholix). Compared to PE, Cholix has a slightly larger theoretical MW (70703.89 Da) and a slightly more acidic theoretical pI (5.12). The crystal structure of the 634 amino acid Cholix protein has been resolved to ~2 Å. The domain structure and organization was found to be somewhat similar to PE: domain I ($Val^1$-$Lys^{265}$), domain II ($Gly^{266}$-$Ala^{386}$), domain III ($Arg^{426}$-$Lys^{634}$), and a Ib loop ($Ala^{387}$-$Asn^{425}$). Additional structural similarity to PE includes: a furin protease site for cellular activation; a C-terminal KDEL sequence that can route the toxin to the endoplasmic reticulum of the host cell; and an ADP-ribosyltransferase activity site within domain III.

Remarkably, PE and Cholix share no significant genetic and limited similarity by amino acid alignment. Searching the genome of *V. cholera* for PE-like nucleotide sequences fails to result in a match of any kind. It is only at the protein sequence level is there the hint that an PE-like protein could be produced by this bacterium. Even here, there is only a 32% homology between the amino acid sequences of PE and Cholix with similarities (42% homology) being focused in the ADP ribosylation elements of domain III, and with low levels of amino acid homology (~15-25%) for most segments of domains I and II for the two proteins. Moreover, this overall arrangement of Cholix relative to PE is even more striking since these two proteins with similar elements were derived from two distinct directions: *P. aeruginosa* is a GC-rich bacterium while *V. cholera* is AT-rich. That these two toxins evolved from two different genetic directions to arrive at nearly the same structure but with only 32% amino acid homology suggests that structural and functional similarities of Cholix and PE are likely based upon similar survival pressures rather than through similar genetic backgrounds. The very low amino acid homology of domains I and II for these two proteins stress the functional importance of the folded structures of these two proteins and not their amino acid sequences.

The C-terminal portion of Cholix and PE appear to function in the intoxication of cells through ADP-ribosylation of EF2 in comparable ways. Recent studies where the latter half of Cholix (domain I deleted) targeted to cancer cells through conjugation to an antibody directed to the transferrin receptor suggests that the C-terminal portions of PE and Cholix involved in ADP-ribosylation of EF2 are indeed functionally similar; Sarnovsky, R., et al., *Cancer Immunol Immunother* 59:737-746 (2010). While this distal portion of Cholix is 36% identical and 50% similar to PE, polyclonal antisera raised in animals as well as sera from patients having neutralizing immune responses to this same distal portion of PE failed to cross-react with this latter portion of Cholix. Similarly, antisera raised to this Cholix failed to cross-react with PE. This data suggests that while both PE and Cholix share a capacity to intoxicate cells through a similar mechanism and that these two proteins share a common core structure, there are striking differences in their elements that are expressed at the surface of these proteins.

As previous studies using PE have demonstrated that this toxin readily transports across polarized monolayers of epithelial cells in vitro and in vivo without intoxication; Mrsny, R. J., et al., *Drug Discov Today*, 7(4): p. 247-58 (2002), the present inventors have commenced research to further evaluate the properties and biology of Cholix, with a particular focus on the functional aspects of the proximal portions of Cholix; specifically, the use of domains I and II to facilitate transport across intestinal epithelial monolayers. As domains I and IIa appeared to be the only essential elements of PE required for epithelial transcytosis, it was particularly important to examine these same domains in Cholix. As stated previously, there is only ~15%-25% amino acids homology over most of the regions that would be considered to be part of domains I and IIa. The present inventors examined the domains though a series of studies: monitoring the biological distribution of Cholix following application to epithelial surfaces in vivo, assessment of Cholix transcellular transport characteristics across polarized epithelial cell monolayers in vitro, and delivery of a biologically-active cargo genetically integrated into the Cholix protein at its C-terminus. Preliminary data generated by genetically fusing the first two domains of Cholix (amino acids 1-386) to green fluorescent protein (GFP) or chemically coupling these expressed domains to 100 nm diameter latex beads demonstrated that Cholix attached to 100 nm latex beads were observed to transport across intestinal epithelial monolayers in vitro and in vivo. That the GFP cargo retained its fluorescent character during and after the transcytosis process also support the contention that Cholix utilizes a non-destructive (or privileged) trafficking pathway through polarized epithelial cells. This outcome bodes well for its (repeated) application as a tool to deliver biologically active cargos across epithelial barriers of the body, such as those in the respiratory and gastrointestinal tracts.

Also of important note from the preliminary studies is the observation which suggests an apparent cell receptor interaction difference between PE and Cholix. As stated previously, PE enters into epithelial cells after domain I of PE binds to the membrane protein α2-macroglobulin, a protein which is also known as the low-density lipoprotein receptor-related protein 1 (LRP1) or CD91. While the exact identity of the surface receptor for Cholix has not been established, preliminary studies suggest that Cholix does not intoxicate some cell lines that express CD91 but intoxicates some cell lines that do express CD91. It is currently unclear what other receptors, beyond CD91, might be involved epithelial transcytosis of PE. Nevertheless, Cholix and PE appear to have distinct cell receptor interactions, demonstrating clear differences that are sufficient to suggest very different and unanticipated applications for both oral biologics and the intracellular delivery of bioactive agents.

DISCLOSURE OF INVENTION

The present invention is based on the membrane-trafficking properties of Cholix and the demonstration that Cholix transports efficiently across polarized epithelial cells of the airway and intestine, suggesting that Cholix-derived polypeptide sequences (including the proximal elements of the protein) can be used for the efficient transcytosis of protein and nanoparticles, representing a strategy for novel pharmaceutical applications.

As such, one aspect of the present invention is to provide isolated delivery constructs (e.g., genetic fusions or chemical constructs) comprising a transporter domain (e.g., a Cholix-derived polypeptide sequence) and a cargo. Both the transport domain and cargo may be expressed/linked in varying stoichiometric ratios and spatial organization. Different cargos may also be expressed/linked on the same construct. In preferred embodiments such cargo may include one, or any of: proteins, peptides, small molecules, siRNA, PNA, miRNA, DNA, plasmid, and antisense.

Another aspect of the present invention is to provide for the ability to deliver cargo, such as macromolecules, without injections.

Another aspect of the present invention is to provide for the ability to deliver cargo, such as (but not limited to) macromolecules, small molecules, siRNA, PNA, miRNA, DNA, plasmid and antisense molecules, into intracellular compartments where their activity is required.

Another aspect of the present invention is to provide for the transport of cargo via delivery of nanoparticles and/or dendrimer-based carriers across biological membranes.

Methods of administration/delivery contemplated for use in the present invention include, e.g., oral administration, pulmonary administration, intranasal administration, buccal administration, sublingual administration, ocular administration (including, but not limited to, delivery to the vitreous, cornea, conjunctiva, sclera, and posterior and anterior compartments of the eye), topical application, injection (needle or needle-free), intravenous infusion, microneedle application, administration via a drug depot formulation, administration via intrathecal application, administration via intraperitoneal application, administration via intra-articular application, delivery intracellularly, delivery across blood brain barrier, delivery across blood retina barrier, administered for local delivery and action, and/or delivered for systemic delivery.

In yet another aspect, the invention provides a pharmaceutical composition comprising the delivery constructs and a pharmaceutically acceptable carrier.

BRIEF DESCRIPTION OF DRAWINGS

FIG. 1 depicts an overview of the strategy used for the C-terminal modification of ntCholix to facilitate fusion with a cargo, in this instance, the cargo being Alexa488 flourescent dye.

FIG. 2 depicts the transport of ntCholix-Alexa488® across polarized intestinal epithelial cells in vitro. Caco-2 cell monolayers were exposed to test materials for 4 hr. The percentage of material transported was determined by standard curve analysis of fluorescence present in the samples and presented as an average (N=4). BSA-Alexa488 was used as a control.

MODE(S) FOR CARRYING OUT THE INVENTION

As those in the art will appreciate, the foregoing description describes certain preferred embodiments of the invention in detail, and is thus only representative and does not depict the actual scope of the invention. It is also to be understood that the terminology used herein is for the purpose of describing particular embodiments only, and is not intended to limit the scope of the invention defined by the appended claims.

Unless defined otherwise, all technical and scientific terms used herein have the meaning commonly understood by a person skilled in the art to which this invention belongs. As used herein, the following terms have the meanings ascribed to them unless specified otherwise.

The studies underlying the present invention relate to the use of Cholix-derived polypeptide sequences as the transporter domain to be used to prepare isolated delivery constructs to enhance intestinal delivery of biologically-active therapeutics. Importantly, the systems and methods described herein provide for the following: the ability to deliver macromolecule doses without injections; the ability to deliver "cargo" into intracellular compartments where their activity is required; and the delivery of nanoparticles and/or dendrimer-based carriers across biological membranes, which otherwise would have been impeded due to the barrier properties of most such membranes.

Mature Cholix toxin ("Cholix") is an extremely active monomeric protein (molecular weight 70 kD) secreted by *Vibrio cholerae*, and which is composed of three prominent globular domains (Ia, II, and III) and one small subdomain (Ib) that connects domains II and III. The amino acid sequence of mature Cholix is provided in Jorgensen, R. et al., *J Biol Chem*, 283(16):10671-10678 (2008) and references cited therein. The Cholix-derived polypeptide sequences used in the preparation of the isolated delivery constructs of the present invention will be derived from the reported 634 amino acid protein sequence of mature Cholix.

Accordingly, the delivery constructs of the present invention comprise a transporter domain. A "transporter domain" as used herein refers to structural domains which are capable of performing certain functions, e.g., cell recognition (i.e., comprise a receptor binding domain) and transcytosis (i.e., comprise a transcytosis domain). Generally, the transporter domains to be used in the preparation of the delivery constructs of the present invention are Cholix-derived polypeptide sequences that have structural domains corresponding to the functional domains, e.g., Ia and II, of Cholix.

In addition to the portions of the molecule that correspond to Cholix functional domains, the delivery constructs of this invention can further comprise a macromolecule for delivery to a biological compartment of a subject. In certain embodiments, the macromolecule is selected from the group of a nucleic acid, a peptide, a polypeptide, a protein, a polysaccharide, and a lipid. In further embodiments, the polypeptide is selected from the group consisting of polypeptide hormones, cytokines, chemokines, growth factors, and clotting factors that are commonly administered to subjects by injection. The sequences of all of these macromolecules are well known to those in the art, and attachment of these macromolecules to the delivery constructs is well within the skill of those in the art using standard techniques.

The macromolecule can be introduced into any portion of the delivery construct that does not disrupt a cell-binding or transcytosis activity. The macromolecule is connected to the remainder of the delivery construct through a cleavable linker. "Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, changes in temperature, pH, salt concentration, etc. when there is such a change in environment following transcytosis of the delivery construct across a polarized epithelial membrane.

In certain embodiments, the delivery constructs further comprise a second macromolecule that is selected from the group consisting of a nucleic acid, a peptide, a polypeptide, a protein, a lipid, and a small organic molecule and a second cleavable linker, wherein cleavage at said second cleavable linker separates said second macromolecule from the remainder of said construct. In certain embodiments, the first macromolecule is a first polypeptide and said second macromolecule is a second polypeptide. In certain embodiments, the first polypeptide and the second polypeptide associate to form a multimer. In certain embodiments, the multimer is a dimer, tetramer, or octamer. In further embodiments, the dimer is an antibody.

In certain embodiments, the macromolecule can be selected to not be cleavable by an enzyme present at the basal-lateral membrane of an epithelial cell. For example, the assays described in the examples can be used to routinely test whether such a cleaving enzyme can cleave the macromolecule to be delivered. If so, the macromolecule can be routinely altered to eliminate the offending amino acid sequence recognized by the cleaving enzyme. The altered macromolecule can then be tested to ensure that it retains activity using methods routine in the art.

In certain embodiments, the first and/or the second cleavable linker is cleavable by an enzyme that exhibits higher activity on the basal-lateral side of a polarized epithelial cell than it does on the apical side of the polarized epithelial cell. In certain embodiments, the first and/or the second cleavable linker is cleavable by an enzyme that exhibits higher activity in the plasma than it does on the apical side of a polarized epithelial cell.

In certain embodiments, the cleavable linker can be selected based on the sequence, in the case of peptide, polypeptide, or protein macromolecules for delivery, to avoid the use of cleavable linkers that comprise sequences present in the macromolecule to be delivered. For example, if the macromolecule comprises AAL, the cleavable linker can be selected to be cleaved by an enzyme that does not recognize this sequence.

In addition to the portions of the molecule that correspond to Cholix functional domains, the delivery constructs of this invention can further comprise a "cargo" for delivery into intracellular compartments where their activity is required. A "cargo" as used herein includes, but is not limited to: macromolecules, small molecules, siRNA, PNA, miRNA, DNA, plasmid and antisense molecules. Other examples of cargo that can be delivered according to the present invention include, but are not limited to, antineoplastic compounds, such as nitrosoureas, e.g., carmustine, lomustine, semustine, strepzotocin; methylhydrazines, e.g., procarbazine, dacarbazine; steroid hormones, e.g., glucocorticoids, estrogens, progestins, androgens, tetrahydrodesoxycaricosterone; immunoactive compounds such as immunosuppressives, e.g., pyrimethamine, trimethopterin, penicillamine, cyclosporine, azathioprine; and immunostimulants, e.g., levamisole, diethyl dithiocarbamate, enkephalins, endorphins; antimicrobial compounds such as antibiotics, e.g., .beta.-lactam, penicillin, cephalosporins, carbapenims and monobactams, .beta.-lactamase inhibitors, aminoglycosides, macrolides, tetracyclins, spectinomycin; antimalarials, amebicides; antiprotazoals; antifungals, e.g., amphotericin .beta., antivirals, e.g., acyclovir, idoxuridine, ribavirin, trifluridine, vidarbine, gancyclovir; parasiticides; antihalmintics; radiopharmaceutics; gastrointestinal drugs; hematologic compounds; immunoglobulins; blood clotting proteins, e.g., antihemophilic factor, factor IX complex; anticoagulants, e.g., dicumarol, heparin Na; fibrolysin inhibitors, e.g., tranexamic acid; cardiovascular drugs; peripheral anti-adrenergic drugs; centrally acting antihypertensive drugs, e.g., methyldopa, methyldopa HCl; antihypertensive direct vasodilators, e.g., diazoxide, hydralazine HCl; drugs affecting renin-angiotensin system; peripheral vasodilators, e.g., phentolamine; anti-anginal drugs; cardiac glycosides; inodilators, e.g., amrinone, milrinone, enoximone, fenoximone, imazodan, sulmazole; antidysrhythmics; calcium entry blockers; drugs affecting blood lipids, e.g., ranitidine, bosentan, rezulin; respiratory drugs; sypathomimetic drugs, e.g., albuterol, bitolterol mesylate, dobutamine HCl, dopamine HCl, ephedrine So, epinephrine, fenfluramine HCl, isoproterenol HCl, methoxamine HCl, norepinephrine bitartrate, phenylephrine HCl, ritodrine HCl; cholinomimetic drugs, e.g., acetylcholine Cl; anticholinesterases, e.g., edrophonium Cl; cholinesterase reactivators; adrenergic blocking drugs, e.g., acebutolol HCl, atenolol, esmolol HCl, labetalol HCl, metoprolol, nadolol, phentolamine mesylate, propanolol HCl; antimuscarinic drugs, e.g., anisotropine methylbromide, atropine SO.sub.4, clinidium Br, glycopyrrolate, ipratropium Br, scopolamine HBr; neuromuscular blocking drugs; depolarizing drugs, e.g., atracurium besylate, hexafluorenium Br, metocurine iodide, succinylcholine Cl, tubocurarine Cl, vecuronium Br; centrally acting muscle relaxants, e.g., baclofen; neurotransmitters and neurotransmitter agents, e.g., acetylcholine, adenosine, adenosine triphosphate; amino acid neurotransmitters, e.g., excitatory amino acids, GABA, glycine; biogenic amine neurotransmitters, e.g., dopamine, epinephrine, histamine, norepinephrine, octopamine, serotonin, tyramine; neuropeptides, nitric oxide, K.sup.+channel toxins; antiparkinson drugs, e.g., amaltidine HCl, benztropine mesylate, carbidopa; diuretic drugs, e.g., dichlorphenamide, methazolamide, bendroflumethiazide, polythiazide; antimigraine drugs, e.g, carboprost tromethamine mesylate, methysergide maleate. The transporter domains of the delivery constructs of the present invention generally comprise a receptor binding domain. The receptor binding domain can be any receptor binding domain known to one of skill in the art without limitation to bind to a cell surface receptor that is present on the apical membrane of an epithelial cell. Preferably, the receptor binding domain binds specifically to the cell surface receptor. The receptor binding domain should bind to the cell surface receptor with sufficient affinity to allow endocytosis of the delivery construct.

In certain embodiments, the receptor binding domain can comprise a peptide, a polypeptide, a protein, a lipid, a carbohydrate, or a small organic molecule, or a combination thereof. Examples of each of these molecules that bind to cell surface receptors present on the apical membrane of epithelial cells are well known to those of skill in the art. Suitable peptides or polypeptides include, but are not limited to, bacterial toxin receptor binding domains, such as the receptor binding domains from PE, cholera toxin, Cholix toxin, botulinum toxin, diptheria toxin, shiga toxin, shiga-like toxin, etc.; antibodies, including monoclonal, polyclonal, and single-chain antibodies, or derivatives thereof, growth factors, such as EGF, IGF-I, IGF-II, IGF-III etc.; cytokines, such as IL-1, IL-2, IL-3, IL-6, etc; chemokines, such as MIP-1a, MIP-1b, MCAF, IL-8, etc.; and other ligands, such as CD4, cell adhesion molecules from the immunoglobulin superfamily, integrins, ligands specific for the IgA receptor, etc. The skilled artisan can select the appropriate receptor binding domain based upon the expression pattern of the receptor to which the receptor binding domain binds.

The receptor binding domain can be attached to the remainder of the delivery construct by any method or means known by one of skill in the art to be useful for attaching such molecules, without limitation. In certain embodiments, the receptor binding domain is expressed together with the remainder of the delivery construct as a fusion protein. Such embodiments are particularly useful when the receptor binding domain and the remainder of the construct are formed from peptides or polypeptides.

The transporter domains of the delivery constructs of the present invention further comprise a transcytosis domain. The transcytosis domain can be any transcytosis domain known by one of skill in the art to effect transcytosis of chimeric proteins that have bound to a cell surface receptor present on the apical membrane of an epithelial cell. In preferred embodiments, the transcytosis domain is domain II of Cholix.

Without intending to be limited to any particular theory or mechanism of action, the transcytosis domain is believed to permit the trafficking of the delivery construct through a polarized epithelial cell after the construct binds to a receptor present on the apical surface of the polarized epithelial cell. Such trafficking through a polarized epithelial cell is referred to herein as "transcytosis." This trafficking permits the release of the delivery construct from the basal-lateral membrane of the polarized epithelial cell.

For the delivery of cargo intended for intracellular activity, the delivery construct comprises an endocytosis domain to traffic the cargo into the cell, and may also comprise a cleavable linker. This includes the intracellular delivery of cargo using nanoparticle and/or dendrimer-based carriers targeted to the cell surface receptor by decorating the carrier surface with one or more copies of the endocytosis domain, with or without the use of linkers.

Without intending to be limited to any particular theory or mechanism of action, the endocytosis domain is believed to permit the trafficking of the delivery construct into a cell after the construct binds to a receptor present on the surface of the cell. Such trafficking into a cell is referred to herein as "endocytosis". This trafficking permits the release of the delivery construct into the relevant intracellular compartment, including (but not limited to) the nucleus and nuclear envelope, ribosomal vesicles, endoplasmic reticulum, mitochondria, golgi apparatus, and cytosol.

In certain embodiments of the present invention, identification of proteases and peptidases that function biological processes that occur at the basolateral surface of these cells will be evaluated. These proteases and peptidases would fall into several categories that can be defined by their substrates: 1) pre-pro-hormones and enzymes that are secreted from epithelial basolateral surfaces and required trimming for their activation, 2) active hormones or enzymes whose activity is neutralized by a cleavage event in order to regulate their activity, and 3) systemic enzymes or growth factors whose actions at the basolateral surface are altered by enzymatic modification. Examples of several potential activities that fall into these various categories and which might be of useful for the basolateral cleavage of carrier-linker-cargo constructs include members of the S9B prolyl oligopeptidase subfamily, e.g., FAP and DDP IV, which have been described in the art.

The nucleic acid sequences and polynucleotides of the present invention can be prepared by any suitable method including, for example, cloning of appropriate sequences or by direct chemical synthesis by methods such as the phosphotriester method of Narang, et al., *Meth. Enzymol*., 68:90-99 (1979); the phosphodiester method of Brown, et al., *Meth. Enzymol*., 68:109-151 (1979); the diethylphosphoramidite method of Beaucage, et al., *Tetra. Lett*., 22:1859-1862 (1981); the solid phase phosphoramidite triester method described by Beaucage & Caruthers, *Tetra. Letts*., 22(20): 1859-1862 (1981), e.g., using an automated synthesizer as described in, for example, Needham-VanDevanter, et al. *Nucl. Acids Res*. 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Cells suitable for replicating and for supporting recombinant expression of protein are well known in the art. Such cells may be transfected or transduced as appropriate with the particular expression vector and large quantities of vector containing cells can be grown for seeding large scale fermenters to obtain sufficient quantities of the protein for clinical applications. Such cells may include prokaryotic microorganisms, such as *E. coli*; various eukaryotic cells, such as Chinese hamster ovary cells (CHO), NSO, 292; Yeast; insect cells; and transgenic animals and transgenic plants, and the like. Standard technologies are known in the art to express foreign genes in these systems.

The pharmaceutical compositions of the present invention comprise a genetic fusion or chemical construct of the invention and a pharmaceutically acceptable carrier. As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. Except insofar as any conventional excipient, carrier or vehicle is incompatible with the delivery constructs of the present invention; its use in the pharmaceutical preparations of the invention is contemplated.

In certain embodiments, the pharmaceutical compositions of active compounds may be prepared with a carrier that will protect the composition against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems (J. R. Robinson, ed., Marcel Dekker, Inc., New York, 1978).

In certain embodiments, the delivery constructs of the invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the delivery constructs can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Generally, a pharmaceutically effective amount of the delivery construct of the invention is administered to a subject. The skilled artisan can readily determine if the dosage of the delivery construct is sufficient to deliver an effective amount of the macromolecule, as described below. In certain embodiments, between about 1 .mu.g and about 1 g of delivery construct is administered. In other embodiments, between about 10 .mu.g and about 500 mg of delivery construct is administered. In still other embodiments, between about 10 .mu.g and about 100 mg of delivery construct is administered. In yet other embodiments, between about 10 .mu.g and about 1000 .mu.g of delivery construct is administered. In still other embodiments, between about 10 .mu.g and about 250 .mu.g of delivery construct is administered. In yet other embodiments, between about 10 .mu.g and about 100 .mu.g of delivery construct is administered. Preferably, between about 10 .mu.g and about 50 .mu.g of delivery construct is administered.

The delivery constructs of the invention offer several advantages over conventional techniques for local or systemic delivery of macromolecules to a subject. Foremost among such advantages is the ability to deliver the macromolecule without using a needle to puncture the skin of the subject. Many subjects require repeated, regular doses of macromolecules. For example, diabetics must inject insulin several times per day to control blood sugar concentrations. Such subjects' quality of life would be greatly improved if the delivery of a macromolecule could be accomplished without injection, by avoiding pain or potential complications associated therewith.

Furthermore, many embodiments of the delivery constructs can be constructed and expressed in recombinant systems. Recombinant technology allows one to make a delivery construct having an insertion site designed for introduction of any suitable macromolecule. Such insertion sites allow the skilled artisan to quickly and easily produce delivery constructs for delivery of new macromolecules, should the need to do so arise.

In addition, connection of the macromolecule to the remainder of the delivery construct with a linker that is cleaved by an enzyme present at a basal-lateral membrane of an epithelial cell allows the macromolecule to be liberated from the delivery construct and released from the remainder of the delivery construct soon after transcytosis across the epithelial membrane. Such liberation reduces the probability of induction of an immune response against the macromolecule. It also allows the macromolecule to interact with its target free from the remainder of the delivery construct.

Other advantages of the delivery constructs of the invention will be apparent to those of skill in the art.

Example 1

A plasmid construct was prepared encoding mature *Vibrio cholera* Cholix and used to express the mature Cholix protein in an *E. coli* expression system as previously described; see, e.g., Jorgensen, R. et al., *J Biol Chem*, 283(16):10671-10678 (2008). A non-toxic mutant form of the Cholix gene (hereinafter referred to as "ntCholix") was also prepared by genetic deletion of a glutamic acid at amino acid position 581 (ΔE581) which is analogous to a deletion (ΔE553) in the PE protein that renders it non-toxic without significantly altering its conformation; Killeen, K. P. and Collier, R. J., *Biochim Biophys Acta*, 1138:162-166 (1992). Protein expression was achieved using *E. coli* DH5α cells (Invitrogen, Carlsbad, Calif.) following transformation by heat-shock (1 min at 42° C.) with the appropriate plasmid. Transformed cells, selected on antibiotic-containing media, were isolated and grown in Luria-Bertani broth (Difco). Protein expression was induced by addition of 1 mM isopropyl-D-thiogalactopyranoside (IPTG). Two hours following IPTG induction, cells were harvested by centrifugation at 5,000×g for 10 min at 4° C. Inclusion bodies were isolated following cell lysis and proteins were solubilized in 6 M guanidine HCl and 2 mM EDTA (pH 8.0) plus 65 mM dithiothreitol. Following refolding and purification, proteins were stored at ~5 ml/ml in PBS (pH 7.4)

lacking $Ca^{2+}$ and $Mg^{2+}$ at −80° C. All proteins used in these studies were confirmed to be at >90% purity based upon size exclusion chromatography.

Figure 1:
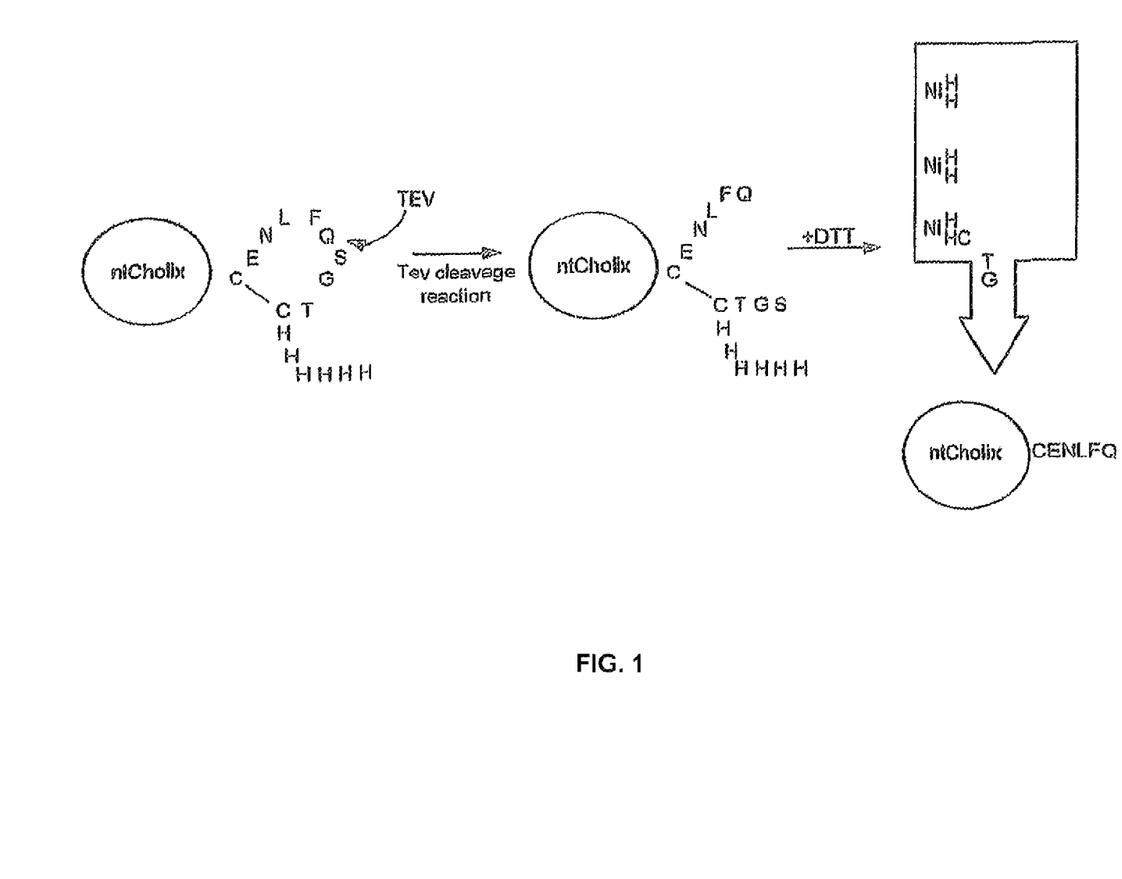
Figure 2:
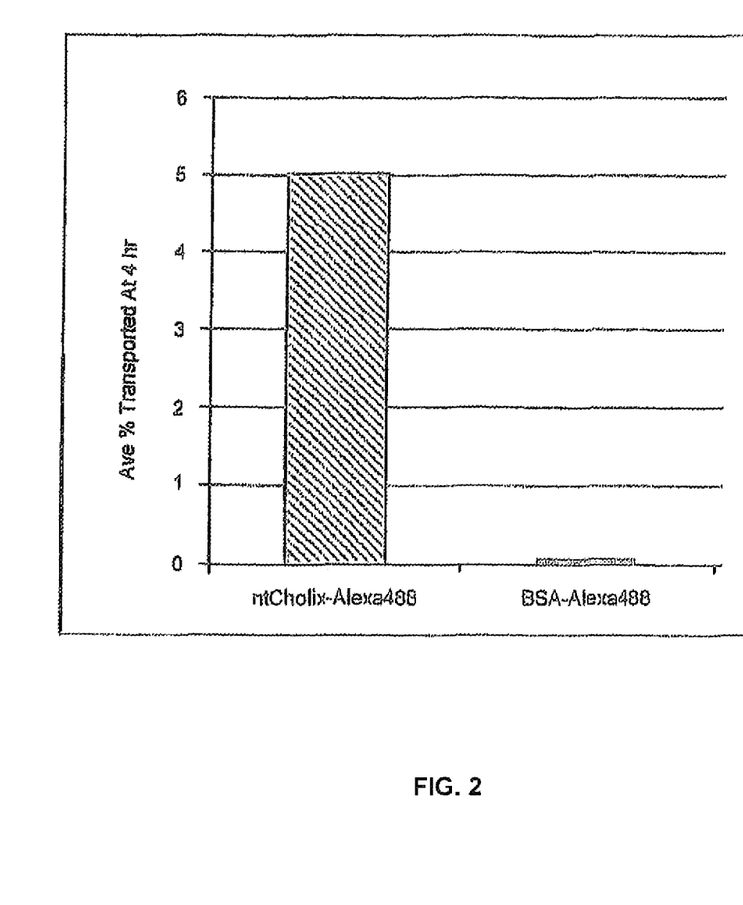

The ntCholix form was then modified at its C-terminus to allow direct chemical coupling through a free sulfhydryl residue located near the C-terminus of the protein. The strategy for the C-terminal modification is depicted in FIG. 1. The C-terminal modification included a cysteine-constrained loop harboring the consensus cleavage sequence (ENLFQS) for the highly selective protease from the tobacco etch virus (TEV), a second cysteine, and a hexa-histidine ($His_6$) tag. The second Cys was included to form a disulphide bridge with the Cys ultimately used for coupling. Adding the $His_6$ sequence to the protein simplified the purification and the TEV cleavage sequence provided a mechanism to selectively remove the terminal Cys residue following mild reduction. TEV cleavage and mild reduction with 0.1 mM dithiotheitol following expression and isolation of the ntCholix constructs allowed for the direct chemical coupling of a cargo, Alexa Fluor® 488 fluorescent dye, via a maleimide-based reaction as a generic mechanism of cargo attachment. The resultant construct is referred to herein as ntCholix-Alexa488. Following TEV protease cleavage, reduction, and cargo coupling through a maleimide reaction with the free sulfhydryl, removal of the freed C-terminal sequence was achieved by a second $Ni^{2+}$ column chromatography step.

Example 2

Trans-epithelial transport of ntCholix-Alexa488 was assessed using Caco-2 monolayers in vitro. First, Caco-2 cells (passage number 25-35) were grown to confluent monolayers as previously described; Rubas, W. et al., *Pharm Res*, 10:113-118 (1993). Briefly, cells were maintained at 37° C. in DMEM/high growth media enriched with 2 mM L-glutamine, 10% fetal bovine serum, and 100 Units of penicillin/streptomycin in an atmosphere of 5% $CO_2$ and 90% humidity. Cells were passaged every week at a split ratio of 1:3 in 75 $cm^2$ flasks and seeded onto prewetted and collagen-coated permeable (0.4 μm pore size) polycarbonate (Transwell™) filter supports from Corning Costar (Cambridge, Mass.) at a density of 63,000 cells/$cm^2$. Growth media was replaced every other day. Confluent monolayers, determined by the acquisition of significant trans-epithelial resistance (TEER) determine using an volt-ohm-meter (World Precision Instruments, Sarasota, Fla.), were used 20-26 days post seeding.

Two additional materials were also prepared to be used as controls to assess the in vitro transport of Cholix. As an internal control for filter damage, tetramethylrhodamine isothiocyanate (TRITC)-labeled 70 kDa dextan was obtained from commercial source (Sigma). As a control for non-specific dye-mediated transport we reacted some of the free amines on the surface of bovine serum albumin (BSA; Sigma) with Alexa488 carboxylic acid succinimidyl ester (A488-CASE; Invitrogen). The coupling reaction was carried out for 4 hr at room temperature at neutral pH at a molar ratio of 10:1 A488-CASE:BSA at which point excess glycine was added to quench the reaction. The resulting purified product contained ~3 Alexa488 molecules per BSA molecule. Tetramethylrhodamine isothiocyanate (TRITC)-labeled 70 kDa dextan (Sigma) was used as an internal control for filter damage. Fluorescence measurements were made using a BMG labtech FLUOstar Omega instrument set at 540 nm excitation and 610 nm emission for TRITC-Dextran (optimal Ex=547 and Em=572) and 480 nm excitation and 520 nm emission for Alexa488 proteins (optimal Ex=496 and Em=519).

Trans-epithelial transport flux rates were measured in vitro in the apical (Ap) to basolateral (Bl) and the Bl to Ap directions using polarized monolayers of Caco-2 cells to describe mucosal to serosal and serosal to mucosal flux events, respectively. Just prior to initiation of a transport study, the transepithelial resistance (TEER) of each filter was measured; monolayers TEER reading of <200 Ω·cm2 were excluded from the study. Ap and Bl media was removed from included monolayers and these surfaces were washed with once with phosphate buffered saline (PBS). One set of monolayers then received an Ap (donor) application of 100 μL PBS containing 10 μg ntCholix-A488 and 10 μg TRITC-Dextran or 10 μg BSA-A488 and 10 μg TRITC-Dextran. Receiver (Bl) compartments then received 500 μL PBS to set the $T_0$ for the transport study. Both donor and receiver compartments were sampled after 4 hr of incubation at 37° C. to determine the amount of material transported across the monolayer and the amount retained at the apical surface, respectively.

After 4 hour of exposure we observed ~5% of the material added to the apical surface of these monolayers to be transported (see FIG. 2). Any filters showing levels of 75 kDa TRITC-Dextran in the basal compartment were excluded from the analysis. A control protein of BSA-Alexa488 failed to show any significant levels in the basal compartment over this same 4 hr period (see FIG. 2). The averages of transport were 5.025±1.13% for Cholix and 0.56±0.33 for BSA (N=4). This data establishes that a genetically detoxified form of Cholix can efficiently transport in vitro across polarized monolayers of a human intestinal cancer cell line, Caco-2.

Example 3

Also prepared and expressed in *E. coli*. was a variant of Cholix truncated at amino acid $A^{386}$ ($Cholix^{386}$) as well as a genetic ligation of green fluorescent protein (GFP) at the C-terminus of $Cholix^{386}$ ($Cholix^{386}$GFP). Protein expression was achieved using *E. coli* DH5α cells (Invitrogen, Carlsbad, Calif.) following transformation by heat-shock (1 min at 42° C.) with the appropriate plasmid. Transformed cells, selected on antibiotic-containing media, were isolated and grown in Luria-Bertani broth (Difco). Protein expression was induced by addition of 1 mM isopropyl-D-thiogalactopyranoside (IPTG). Two hours following IPTG induction, cells were harvested by centrifugation at 5,000×g for 10 min at 4° C. Inclusion bodies were isolated following cell lysis and proteins were solubilized in 6 M guanidine HCl and 2 mM EDTA (pH 8.0) plus 65 mM dithiothreitol. Following refolding and purification, proteins were stored at ~5 ml/ml in PBS (pH 7.4) lacking $Ca^{2+}$ and $Mg^{2+}$ at −80° C. $Cholix^{386}$GFP refolding was monitored by acquisition and retention of the fluorescence signature associated with this fluorescent protein; Sample et al., *Chem Soc Rev*, 38(10): p. 2852-64 (2009). Green fluorescent protein (GFP) was purchased from Upstate (Charlottesville, Va.). All proteins used in these studies were confirmed to be at >90% purity based upon size exclusion chromatography.

Polystyrene beads (10 nm diameter) containing a covalently integrated red fluorescent dye with excitation/emission properties of 468/508 nm and having aldehyde surface functional groups (XPR-582) were obtained from Duke Scientific (Palo Alto, Calif.). One hundred μl of XPR-582 beads (at 2% solids) was mixed with approximately 2.5 nmoles GFP or $Cholix^{386}$GFP in a final volume of 200 μl neutral (pH 7.0) phosphate buffered saline (PBS). After 2 hr of gentle rocking at room temperature, 20 μl of a 2 mg/ml solution of bovine serum albumin (BSA; Sigma, St. Louis, Mo.) in PBS was added. Preparations were then dialyzed by three cycles of dilution with PBS and concentration using a 100,000 molecular weight cutoff Microcon filter device from Millipore (Bedford, Mass.). Final preparations of coated beads were at 1% solids.

Example 4

A549 (ATCC CCL-185™), L929 (ATCC CRL-2148™), and Caco-2 (ATCC HTB-37™) cells were maintained in 5% $CO_2$ at 37° C. in complete media: Dulbecco's modified Eagle's medium F12 (DMEM F12) supplemented with 10% fetal bovine serum, 2.5 mM glutamine, 100 U of penicillin/ml, and 100 µg of streptomycin/ml (Gibco BRL, Grand Island, N.Y.). Cells were fed every 2 to 3 days with this media (designated complete medium) and passaged every 5 to 7 days. For assays, cells were seeded into 24- or 96-well plates and grown to confluence.

Caco-2 cells were grown as confluent monolayers on collagen-coated 0.4-µm pore size polycarbonate membrane transwell supports (Corning-Costar, Cambridge, Mass.) and used 18-25 days after attaining a trans-epithelial electrical resistance (TEER) of >250 Ω·cm2 as measured using a chopstick Millicell-ERS® voltmeter (Millipore). Apical to basolateral (A→B) and basolateral to apical (B→A) transport of Cholix or Cholix$^{386}$GFP across these monolayer was determined by measuring the amount of transported protein 4 hr after a 20 µg application at 37° C. TEER measurements and the extent of 10 kDa fluorescent dextran (measured using an HPLC size exclusion protocol) were used to verify monolayer barrier properties during the course of the study. The extent of Cholix transport was determined by titration of collected media in the cell-based cytotoxicity assay. Transported Cholix$^{386}$GFP was measured by enzyme linked immunosorbant assay (ELISA) using anti-GFP antibody for capture and the polyclonal sera to Cholix for detection.

Transport rates across polarized Caco-2 cells monolayers in vitro were comparable for Cholix, ntCholix and Cholix$^{386}$GFP as assess by ELISA format analysis. In the case of Cholix, polarized Caco-2 cells were not intoxicated by the protein when examined for TUNEL detection of apoptosis or lactate dehydrogenase (LDH) release. Importantly, Cholix and Cholix-based protein chimeras were found to transport efficiently from the apical to basolateral surface of Caco-2 monolayers but not in the basolateral to apical direction. These transport rates and directionality were comparable to that previously observed for PE tested in this same format. Additionally, we observed that addition rabbit anti-Cholix antisera failed to block the effective transport of Cholix or Cholix-related proteins across Caco-2 monolayers in vitro.

Confocal fluorescence microscopy was used to examine the nature of Cholix$^{386}$GFP transcytosis across Caco-2 monolayers in vitro. A time course study showed Cholix$^{386}$GFP entering into epithelial cells within 5 minutes of its apical application and transporting through cells to the basolateral region of the cell within 15 minutes. In samples exposed to apical Cholix$^{386}$GFP for 15 minutes with subsequent removal of excess Cholix$^{386}$GFP from the apical chamber, GFP fluorescence was observed to continue in the direction of the basolateral surface of the cell and not back toward the apical surface. This unidirectional movement of Cholix$^{386}$GFP was confirmed by measuring Cholix$^{386}$GFP content in the apical and basolateral compartments over this time course. Application of Cholix$^{386}$GFP at the basolateral surface of Caco-2 monolayers did not show any significant fluorescence entering into the cells, consistent with transport studies. Western blot analysis of transported Cholix, ntCholix and Cholix$^{386}$GFP suggested that these proteins transported without major alterations.

In vitro studies also showed that 100 nm diameter fluorescent latex beads chemically coupled to Cholix$^{386}$GFP efficiently transported across Caco-2 monolayers following an apical application. Latex bead selection with a 100 nm diameter provided a material that could readily fit within the lumen of a 125 nm diameter endosome derived from a clatherin-coated pit. Thus, these studies suggest Cholix$^{386}$GFP-latex beads to move through polarized Caco-2 cells by a mechanism consistent with endosome uptake at the apical cell surface followed by endosome-based intracellular trafficking. Pre-incubation of Cholix$^{386}$GFP-coupled 100 nm diameter fluorescent latex beads with anti-Cholix antisera failed to alter the transport of these beads. A similar amount of GFP chemically coupled to 100 nm diameter fluorescent latex beads did not facilitate the in vitro transport of these particles across Caco-2 monolayers. Confocal fluorescence microscopy studies were consistent with differences observed for in transcytosis latex bead coated with Cholix$^{386}$GFP versus GFP.

The result that Cholix is capable of transporting across polarized epithelial barriers similar to PE is unanticipated. While their structures are similar as suggested by crystallographic analysis, their surfaces amino acid composition is strikingly different; indeed, alignment methods based upon amino acid similarity would not readily match these two proteins. This is important in that the ability of a pathogen-derived protein, such as these two virulence factors, to interact with host cell receptors is presumed to involve surface-expressed amino acid components. As both of these proteins (with their substantially different amino acid sequences) transport efficiently across polarized epithelia, it is highly likely that some other mechanism forms that basis for this transport capacity. It is our contention that the structural relationships shared by PE and Cholix forms the basis of the inherent capacity for their efficient transcytosis. While both PE and Cholix proteins would have the capacity to bind to an apical surface receptor to gain access to endosomal compartments it is more likely that this interaction and the potential for other receptors involved in the intracellular trafficking of these proteins would be based upon conformational structures rather than specific amino acids on the protein surface.

All of the articles and methods disclosed and claimed herein can be made and executed without undue experimentation in light of the present disclosure. While the articles and methods of this invention have been described in terms of preferred embodiments, it will be apparent to those of skill in the art that variations may be applied to the articles and methods without departing from the spirit and scope of the invention. All such variations and equivalents apparent to those skilled in the art, whether now existing or later developed, are deemed to be within the spirit and scope of the invention as defined by the appended claims. All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An isolated delivery construct comprising: a modified Cholix toxin consisting of amino acid residues $Val^1$-$Ala^{386}$ and a therapeutic cargo coupled to the modified Cholix toxin, the isolated delivery construct capable of delivering the therapeutic cargo.

2. The isolated delivery construct according to claim 1, wherein the delivering is without injections.

3. The isolated delivery construct according to any one of claims 1 or 2, further comprising a cleavable linker.

4. The isolated delivery construct according to claim 1, wherein the therapeutic cargo is selected from the group consisting of: macromolecules, small molecules, siRNA, PNA, miRNA, DNA, plasmid and antisense molecules.

5. A pharmaceutical composition comprising an isolated delivery construct according to claim 1 and a pharmaceutically acceptable carrier.

6. The isolated delivery construct according to claim 1, wherein the therapeutic cargo is a cytokine.

7. The pharmaceutical composition according to claim 5 that is for oral administration, topical administration, pulmonary administration, intra-nasal administration, buccal administration, sublingual administration or ocular administration.

8. The pharmaceutical composition according to claim 7 that is for oral administration.

9. The pharmaceutical composition according to claim 5 that is formulated in a capsule or tablet.

10. The pharmaceutical composition according to claim 5, comprising from about 1 μg to about 1 g of the isolated delivery construct.

11. The pharmaceutical composition according to claim 10, wherein the isolated delivery construct is from about 10 μg to about 100 mg.

12. The pharmaceutical composition according to claim 11, wherein the isolated delivery construct is from about 10 μg to about 1000 μg.

* * * * *